(12) United States Patent
Joung (10) Patent No.: US 7,861,576 B2
(45) Date of Patent: Jan. 4, 2011

(54) APPARATUS FOR ANALYZING SAMPLE USING CENTRIFUGAL FORCE AND INERTIA

(75) Inventor: Il Kweon Joung, Gyeonggi-do (KR)

(73) Assignee: Samsung Electro-Mechanics Co., Ltd., Suwon (KR)

( * ) Notice: Subject to any disclaimer, the term of this patent is extended or adjusted under 35 U.S.C. 154(b) by 324 days.

(21) Appl. No.: 12/149,257

(22) Filed: Apr. 29, 2008

(65) Prior Publication Data

US 2008/0276729 A1 Nov. 13, 2008

(30) Foreign Application Priority Data

May 9, 2007 (KR) .................... 10-2007-0045166

(51) Int. Cl.
C12M 1/12 (2006.01)
C12M 1/18 (2006.01)

(52) U.S. Cl. .............. 73/61.56; 73/61.43; 435/287.1; 435/288.4; 435/288.5

(58) Field of Classification Search ..... 73/61.43–61.56; 435/287.1–288.5; 436/43, 45
See application file for complete search history.

(56) References Cited

U.S. PATENT DOCUMENTS

| | | | | |
|---|---|---|---|---|
| 4,999,304 | A * | 3/1991 | Robertson | 436/45 |
| 6,319,469 | B1 * | 11/2001 | Mian et al. | 422/64 |
| 6,620,273 | B2 * | 9/2003 | Dai et al. | 156/89.11 |
| 6,709,869 | B2 * | 3/2004 | Mian et al. | 436/45 |
| 6,806,088 | B2 * | 10/2004 | Howard | 436/45 |
| 6,884,395 | B2 * | 4/2005 | Tooke et al. | 422/64 |
| 6,889,468 | B2 * | 5/2005 | Bedingham et al. | 436/45 |
| 7,032,608 | B2 | 4/2006 | Koeneman et al. | |
| 7,147,362 | B2 * | 12/2006 | Caren et al. | 366/135 |
| 7,148,476 | B2 * | 12/2006 | Andersson et al. | 250/288 |
| 7,290,555 | B2 * | 11/2007 | Koeneman et al. | 137/15.18 |
| 7,322,254 | B2 * | 1/2008 | Bedingham et al. | 73/863.86 |
| 7,332,126 | B2 * | 2/2008 | Tooke et al. | 422/64 |
| D564,667 | S * | 3/2008 | Bedingham et al. | D24/216 |
| 7,347,617 | B2 * | 3/2008 | Pugia et al. | 366/341 |
| 7,435,933 | B2 * | 10/2008 | Bedingham et al. | 219/752 |
| 7,635,585 | B2 * | 12/2009 | Yoo | 435/283.1 |
| 7,678,334 | B2 * | 3/2010 | Bedingham et al. | 422/100 |
| 2002/0168663 | A1 * | 11/2002 | Phan et al. | 435/6 |
| 2003/0197139 | A1 * | 10/2003 | Williams | 251/7 |

FOREIGN PATENT DOCUMENTS

KR 10-2004-0004014 1/2004

OTHER PUBLICATIONS

First page of the Korean Published Application 10-2005-0118651, Publication date Dec. 19, 2005.
First page of the Korean Published Application 10-2006-0034390, Publication date Apr. 24, 2006.
Korean Notice of Allowance issued on Feb. 10, 2009 in corresponding Korean Patent Application 10-2007-0045166.

* cited by examiner

*Primary Examiner*—David A. Rogers

(57) ABSTRACT

A sample analyzing apparatus using centrifugal force and inertia including a rotating body composed of a disk including upper and lower thin-films; a plurality of chambers composed of a polygonal space parts in the rotating body and including apertures on one side corner and a bottom side thereof; paths connected between the apertures of the chambers to transfer fluids mixed or separated in the chambers; sample inputting holes connected to the chambers formed inside of the rotating body through the paths; and balls moving within the chambers.

15 Claims, 6 Drawing Sheets

[FIG. 1]

- Prior Art -

APPARATUS FOR ANALYZING SAMPLE USING CENTRIFUGAL FORCE AND INERTIA

CROSS-REFERENCE TO RELATED APPLICATIONS

This application claims the benefit of Korean Patent Application No. 10-2007-0045166 filed with the Korea Intellectual Property Office on May 9, 2007, the disclosure of which is incorporated herein by reference.

BACKGROUND OF THE INVENTION

1. Field of the Invention

The present invention relates to a sample analyzing apparatus for controlling the flow of a fluid by the movement of a ball using centrifugal force and inertia and, more particularly, to a sample analyzing apparatus using the centrifugal force and inertia to realize the separating or mixing of samples flown in each chamber by opening and closing paths connected to the chambers according to the movement of balls using the centrifugal force in the chambers which is generated by rotating in one direction a rotating body provided therein a plurality of chambers connected through the paths therein.

2. Description of the Related Art

In general, at the time of performing a reaction inspection using an analyzing apparatus for clinical diagnosis including a biochemical reaction, separation and mixing processes of various samples including physiological materials are conducted and most of the separation and mixing processes are carried out by a manual operation.

The automation of the separation and mixing processes has been developed and various types of separation and mixing methods of the sample have been recently adopted so as to reduce dependency on the manual operation of the separation and mixing processes of the samples and to achieve more exact separation and mixing of the samples.

A type using the centrifugal force for the separation and mixing of the samples has been mainly used among them and the type using the centrifugal force can acquire a reduction in size in a structure simpler than in comparison with other apparatuses.

However, the apparatus using the centrifugal force is necessarily provided with a valve playing roles of inputting and cutting off the fluid so as to control the flow of the fluid in the course of the separation and mixing of the fluid flowing therein.

At this time, since the apparatus using the centrifugal force is provided with the valve installed therein with a structure using the centrifugal force, the apparatus has a somewhat complicated technical configuration and has a disadvantage in that it is difficult to elaborately control the fluid by means of the valve.

A sample analyzing apparatus having an invention title of "A NUCLEIC ACID ANALYSIS APPARATUS INCLUDING A MICRO VALVE APPARATUS USING MICRO BEAD" (Korean Patent Publication No. 2005-118651) has been developed in order to solve the disadvantage. A representative form of the conventional sample analyzing apparatus shown in FIG. 1

Figure 1:
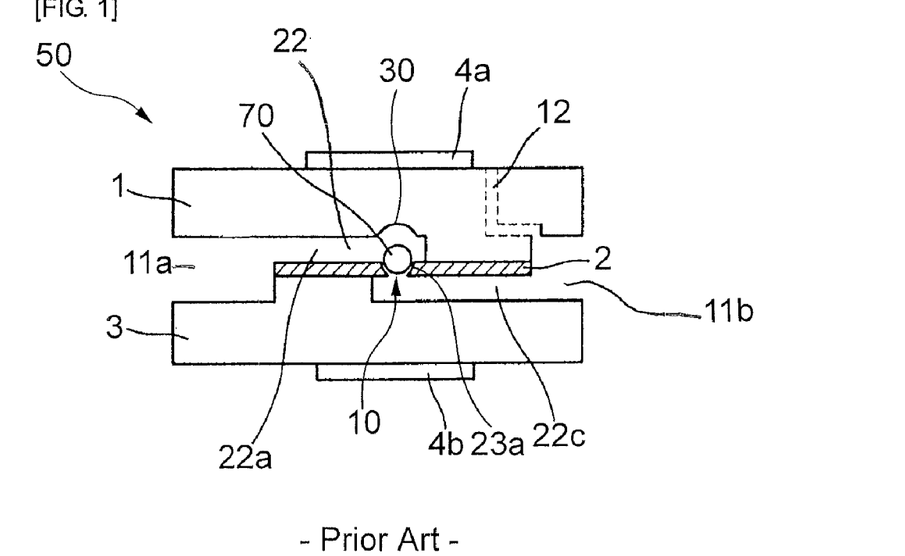
FIG. 1 is a cross-sectional view of a conventional sample analyzing apparatus.

FIG. 1 is a cross-sectional view of a conventional sample analyzing apparatus. As shown in the figure, the conventional sample analyzing apparatus includes a body 50 constituted of an inlet 11a, an outlet 11b, a path 22 including portions 22a and 22c, a vent hole 12, electromagnets 4a and 4b installed at face-to-face positions on top and bottom surfaces of the body 50 to generate magnetic force at the time of applying power, an aperture 10 for connecting the path 22 formed in the inside of the body 50, and a micro bead 70 for controlling the flow of the fluid by opening and the closing the path 10 while moving in a vertical direction by the magnetic force formed by the electromagnets.

Since the path 22 is thin and comparatively narrow, the vent hole 12 is formed so that the fluid transferred in the path 22 can smoothly flow through the path 22.

A restriction groove 30 and a restriction path 23a are formed on the path 22 so that the micro bead 70 is in close contact with an upper substrate 1 and a lower substrate 3. The restriction groove 30 prevents the aperture 10 from being closed due to the separation of the micro bead 70 caused by the vibrations of the substrates. The curvature of the restriction groove 30 is larger than that of an outer circumferential surface of the micro bead 70.

However, in the conventional sample analyzing apparatus, the plural electromagnets 4a and 4b are arranged on the top and bottom surfaces of the body 50 so as to open and close the aperture 10 connected to the path 22 formed in the inside of the body 50. The conventional sample analyzing apparatus is separately provided with the electromagnets 4a and 4b, and electric connecting means and controls circuits for applying the power to the electromagnets 4a and 4b as many as the number of the apertures 10.

Accordingly, many components are consumed for opening and closing the path 22 and an opening/closing structure of the path 22 using the components becomes complicated, thereby increasing manufacturing costs and a failure rate.

Since the vent hole 12 for smoothly transferring the fluid in the path 22 in a direction opposite to the fluid flow or a direction opposite to the centrifugal force is formed in the conventional sample analyzing apparatus, the conventional sample analyzing apparatus has a problem that the fluid may be leaked through the vent hole 12 when the a pressure in a chamber increases.

Although the restriction groove 30 and the restriction path 23a for restricting the movement of the micro bead 70 are formed on top and bottom surfaces of the aperture 10, the micro bead 70 may be separated from the restriction groove 30 and a restriction path 23a, whereby it is difficult to transfer an exact amount of fluids by closing a part of the aperture 10. It is difficult to apply the fluid supply type using the micro bead 70 to the sample analyzing apparatus using the centrifugal force.

SUMMARY OF THE INVENTION

Accordingly, the present invention is invented in order to overcome the above-mentioned disadvantages and problems in the conventional sample analyzing apparatus. It is, therefore, an object of the present invention is that it provides a sample analyzing apparatus using centrifugal force and inertia to realize the separating or mixing of fluids in chambers by controlling the flow of fluids only by the movement of balls according to a rotation direction of a rotating body by opening and closing paths connected to the chambers according to the movement of the balls using the centrifugal force and inertia in the chambers which is generated by rotating in one direction the rotating body provided therein the chambers connected through the paths.

Another object of the present invention is to provide the sample analyzing apparatus using the centrifugal force and inertia including a disk-like rotating body, sample inputting holes formed in the inside of the rotating body, a plurality of chambers having apertures on corners at one side of each of the chambers, paths, paths connected to the apertures of the chambers to transfer fluids in the chambers, and balls moving within the chambers.

The rotating body is composed of a polycarbonate substrate having a reflection coating layer on a surface of the polycarbonate substrate. The rotating body has a form of a disk such as a CD or a DVD. Paths and chambers in which a buffer solution is mixed and stored are formed on a surface of the rotating body.

At this time, the rotating body mixes or separates fluids through the paths connected to the chambers at the time of diagnosing and detecting a small amount of material in the fluid stored in each of the chambers.

The fluids flow between the chambers through the paths for interconnecting the chambers. The paths require valves for controlling the flow and flux of the fluids in the chambers.

At this time, the balls rolled and moved in the chambers serve as the valves for the flux of the fluids in the chambers.

Preferably, the chamber is composed of a triangle, a rectangle, or an oval and corners at one side of the chamber are equipped with corresponding apertures.

The balls moving in the chamber are moved to the corners in the chamber by the centrifugal force generated toward the outer side of the chamber by the rotation of the rotating body and the inertia generated in accordance with masses of the balls at the time of the one-side direction rotation of the rotating body. The aperture is opened or closed while the ball is moved to the corners of each chamber in accordance with a rotation direction of the rotating body.

The paths for allowing the fluids to flow for mixing and separating the samples stored in the chambers are connected through the apertures formed on opposite corners of the chambers when the chambers are connected to each other through the paths in series, whereby the only aperture formed in one chamber is opened by the ball moving in each chamber at the time of the one-side direction of the rotating body.

It is preferable that the chambers are formed in the rotating body having upper and lower thin-film, a height of the path for connecting the chambers is smaller than that of each chamber, and a diameter of the ball rolled and moved in the chamber is smaller than the height of the chamber and is larger than the height of the path.

At this time, upper and lower stepped portions of the path are formed relative to the chamber and a height of the upper stepped portion is smaller than that of the lower stepped portion. Accordingly, the fluid can be smoothly moved at the time when the fluid in the chamber is moved to other chambers through the path.

It is preferable that the ball is made of a material having a mass larger than the fluid so that the ball can be moved at the time when the centrifugal force is activated and a position of the ball is fixed to the corners of each chamber during the centrifugal force is activated.

BRIEF DESCRIPTION OF THE DRAWINGS

Theses and/or other aspects and advantages including a technical configuration of a sample analyzing apparatus using centrifugal force and inertia according to the present invention the present general inventive concept will become apparent and more readily appreciated from the following description of the embodiments, taken in conjunction with the accompanying drawings of which.

DETAILED DESCRIPTION OF THE PREFERRED EMBODIMENTS

Advantages including a technical configuration relative to the above-mentioned objects of a sample analyzing apparatus using centrifugal force and inertia according to the present invention will be clearly understood by detailed description below referring to the accompanying drawings illustrating preferred embodiments of the present invention.

Figure 2:
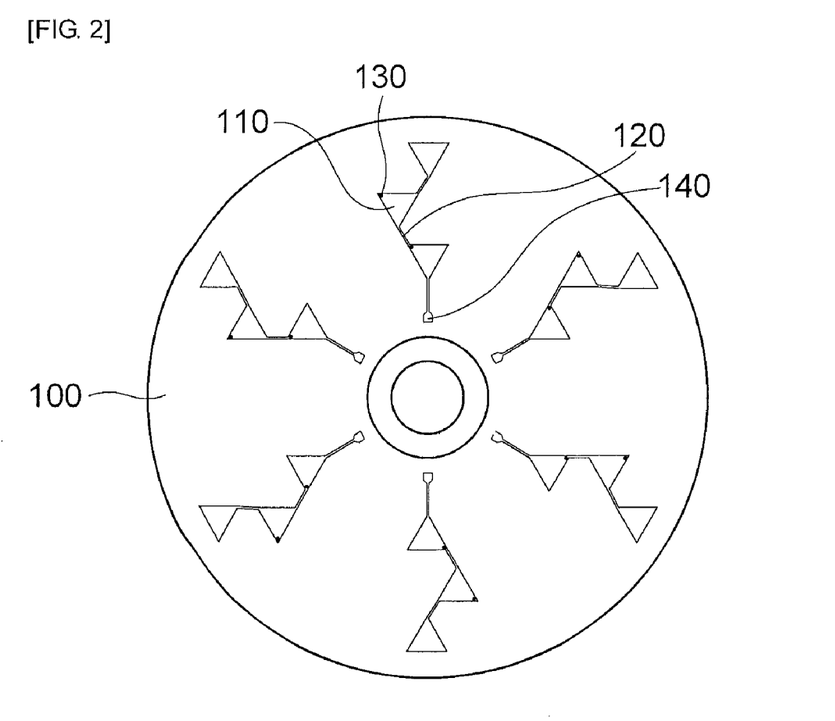
FIG. 2 is a plan view of a sample analyzing apparatus according to the invention.
Figure 3:
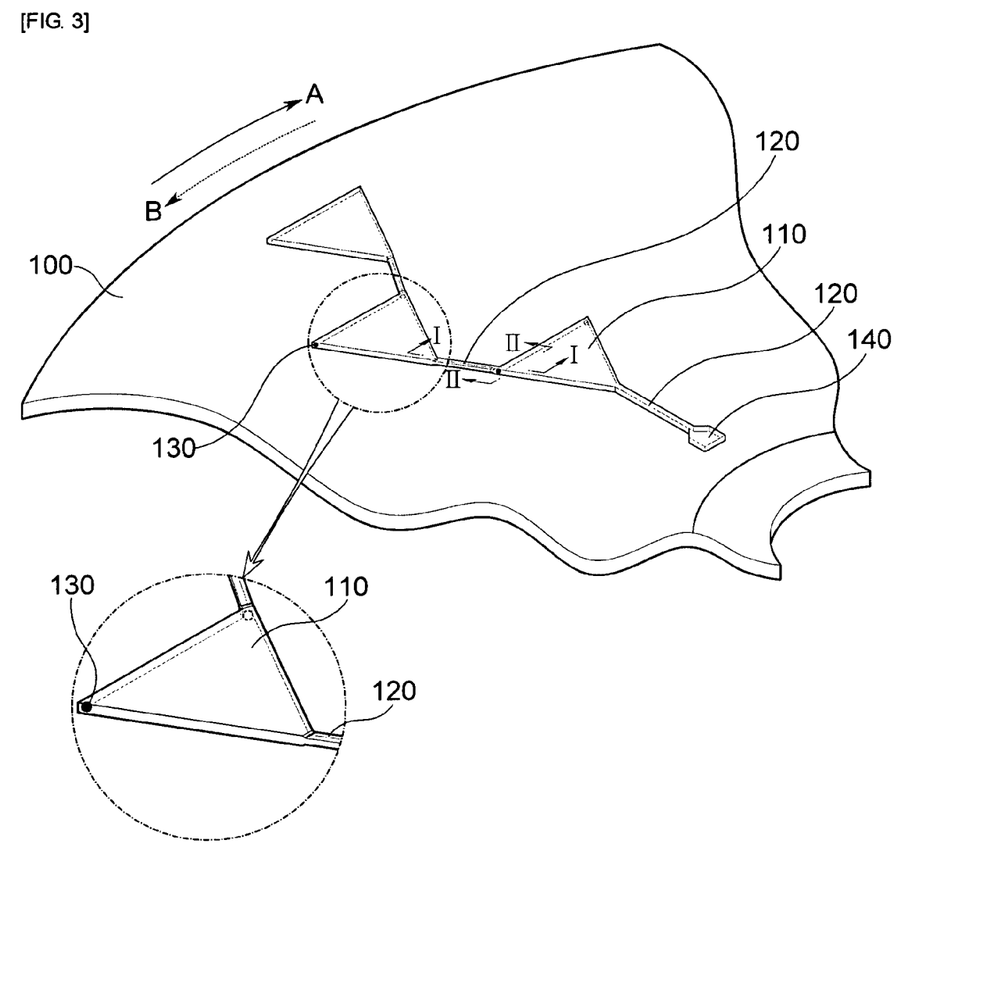
FIG. 3 is a partially expanded perspective view of the sample analyzing apparatus according to the invention.
Figure 4:
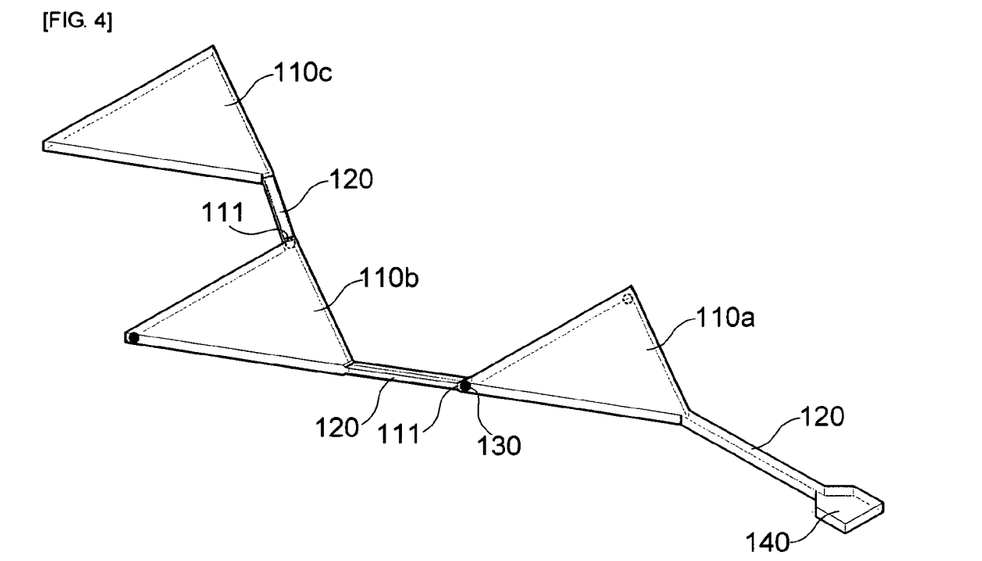
FIG. 4 is an expanded perspective view of a chamber of the sample analyzing apparatus according to the invention.
Figure 5:
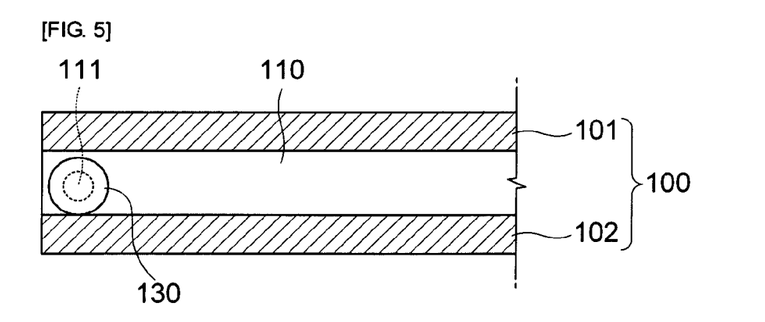
FIG. 5 is a cross-sectional view taken along a line I-I of FIG. 3.
Figure 6:
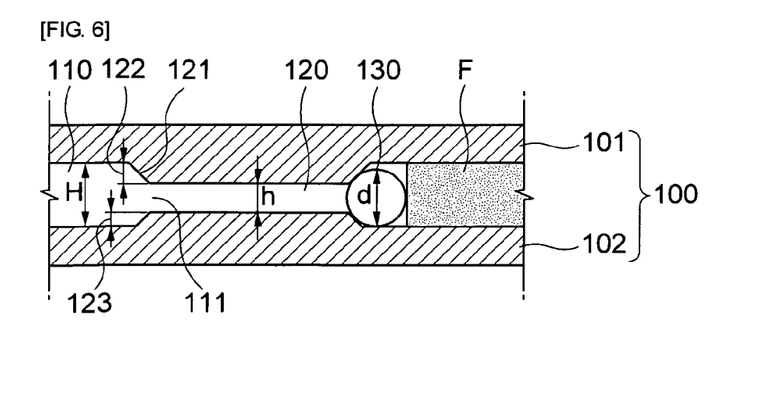
FIG. 6 is a cross-sectional view taken along a line II-II of FIG. 3.

First, FIG. 2 is a plan view of a sample analyzing apparatus according to the invention; FIG. 3 is a partially expanded perspective view of the sample analyzing apparatus according to the invention; FIG. 4 is an expanded perspective view of a chamber of the sample analyzing apparatus according to the invention; FIG. 5 is a cross-sectional view taken along a line I-I of FIG. 3; and FIG. 6 is a cross-sectional view taken along a line II-II of FIG. 3.

As shown in the figures, the sample analyzing apparatus according to the present invention includes a rotating body 100, chambers 110 formed on the rotating body 100 in a space part form, paths 120 for connecting the chambers 110, and balls 130 moving in the chamber 110.

The rotating body 100 is formed in a disk shape and a surface of the rotating body 100 is preferably composed of a polycarbonate substrate in which a reflection coating layer is formed. The rotating body 100 may be globally transparent or parts of the rotating body 100 other than the chambers 110 may be opaque and only chamber forming parts in which a reaction of a sample is measured by mixing or separating the fluids may be transparent.

The rotating body 100 has a form of a disk such as a CD or a DVD in which an upper thin-film and a lower thin-film are overlapped with each other.

The plurality of chambers 110 are formed in the rotating body 100. Each chamber 110 has an aperture 111 on any one of corners thereof and the paths 120 for allowing the fluids in the chambers to flow through the aperture 111 is connected to the chamber 110.

The chamber 110 is formed in a polygon and is composed of a space part having a predetermined height between upper and lower thin-films 101 and 102 constituting the rotating body 100.

At this time, the chamber 110 is preferably formed at an acute angle of 90 degrees or less to fix the ball 130 moving in the chamber 100 at the time of the rotation of the rotating body 100 to corners. Hereinafter, this will be described in more detail with reference to FIG. 5.

The chamber 100a adjacent to the center of the rotating body 100 among the chambers 110 is connected to a sample inputting hole 140 through an additional path 120 and the fluid inputted through the sample inputting hole 140 is transferred to the inside of the chamber 110a along the path 120 at the same time with the rotation of the rotating body 100.

The chamber 110a incorporates the fluid including a measurement sample which is a buffer solution and the ball 130 therein. The fluid F is transferred to other chambers 110 through the path 120 connected to the chamber 110a and the ball 130 moves to the corners of the chamber 110a according to a rotation direction of the rotating body 100 in the chamber 110a.

When the ball 130 moves in the chamber 110, a movement amount of the ball 130 is small relative to centrifugal force in the fluid having high viscosity and is difficult to reach the aperture 111 before the fluid is transferred in case where the ball 130 is inputted into the fluid and moves in the fluid. Therefore, the ball 130 is preferably made of a material having a mass larger than the fluid.

At this time, the path 120 is connected to each chamber 110 in series and the path 120 extends from different corners of the chambers 100 and is opened and closed by the ball 130 moving in the chamber 110 with the rotation of the rotating body 100.

That is, while the ball 130 moves to a corner opposite of the rotation direction of the rotating body 100 at the time of the rotation of the rotating body 100 and therefore the aperture 111 in the chamber 110 is opened or closed by the ball 130, thereby controlling the flow-separation and mix of the fluid.

The ball 130 is moved in the chamber 110 by the centrifugal force generated in the chamber 110 by rotary force of the rotating body 100 and the inertia of the ball 130 at the time of the rotation of the rotating body 100.

As described above, the flow of the fluid through the chamber 110 of the rotating body 100 and the movement of the ball 130 in the chamber 100 will be hereinafter described in more detail.

Herein, the chambers 110 are denoted by a first chamber 110a, a second chamber 110b, and a third chamber 110c from the chamber formed in the inside of the rotating body 100 for convenience in description of a technical configuration of the present invention.

After inputting a liquid fluid containing the sample through the sample inputting hole 140 provided in the inside of the disk-like rotating body 100 formed by joining the upper and lower thin-films 101 and 102, the fluid of the sample inputting hole 140 is transferred to the inside of the first chamber 110a through the path 120 with the rotation of the rotating body 100 in one-side direction (a direction A).

At this time, the balls 130 moving in the first chamber 110a and the second chamber 110b moves to a left corner opposite to the rotation direction of the rotating body 100 in the chambers 110a and 110b by the centrifugal force of the rotating body 100 and the inertia of the ball 130.

Accordingly, the path 120 of the first chamber 110a is closed by the first ball 130 moving in the first chamber 110a, thereby preventing the fluid from flowing to the second chamber 110b.

Moreover, a sample which is a reaction target can be separated from the fluid in the first chamber 110a by centrifugal separation carried out by adjusting a rotation speed of the rotating body 100.

Next, the balls 130 in the first chamber 110a and the second chamber 110b move to right corners of the chambers 110a and 110b opposite to the rotation direction of the rotating body 100 when the rotating body 100 rotates in the other-side direction (a direction B).

At this time, the fluid in the first chamber 110a moves to the second chamber 110b through the path 120 while the aperture 111 of the first chamber 110a is opened, and the aperture 111 of the second chamber 110b to which the path 120 is connected is closed by the second ball 130 moving in the second chamber 110b.

Accordingly, the sample separated from the fluid in the first chamber 110a is moved to and stored in the second chamber 110b.

Finally, the balls 130 in the first chamber 110a and the second chamber 110b move to left sides of the chambers 110a and 110b and the only path connecting the second chamber 110b with the third chamber 110c is opened at the time of rotating the rotating body 100 in the one-side direction (the direction A), where the fluid in the second chamber 110b is transferred to the third chamber 110c.

A biological reaction of the fluid transferred to the third chamber 110c is detected with the fluid transferred to the third chamber 110c being in contact with a surface of a biosensor (not shown in the figure) using an optical wave guide installed in the third chamber 110c.

Meanwhile, as described above, the fluid transferred through the chamber 110 can be mixed and separated by adjusting the rotation speed of the rotating body 100. The path 120 can be opened and the fluid can be mixed by the proper rotation speed to fix the ball 130 to the corner and partial components of the fluid can be separated by the centrifugal separation and can be moved through the path with a rotation speed to centrifugally separate the fluid in the chamber.

As described above, the ball 130 serves as a valve for opening and closing the path by moving to each corner in the chamber 110 according to the rotation direction of the rotating body 100.

Figure 7A:
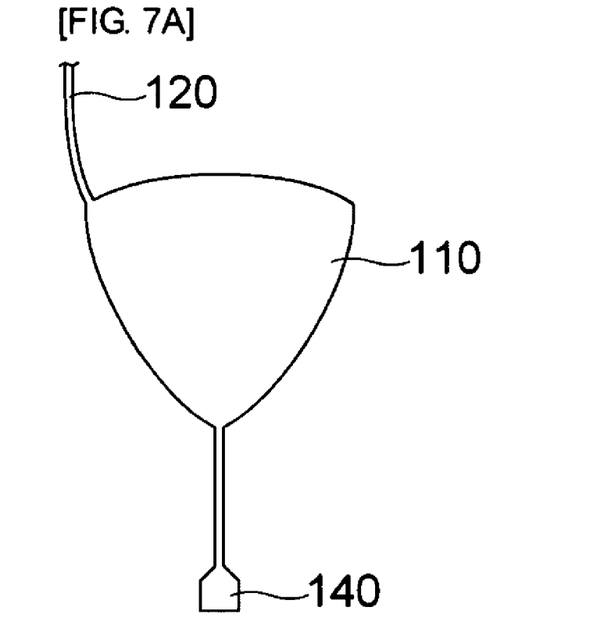
FIGS. 7A to 7C are plan views illustrating a type of a chamber which can be applied to the sample analyzing apparatus according to the invention.
Figure 7B:
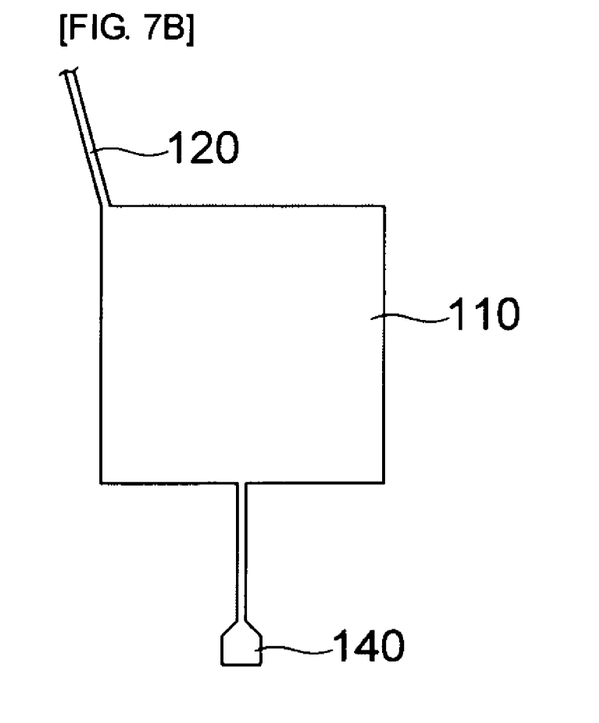
Figure 7C:
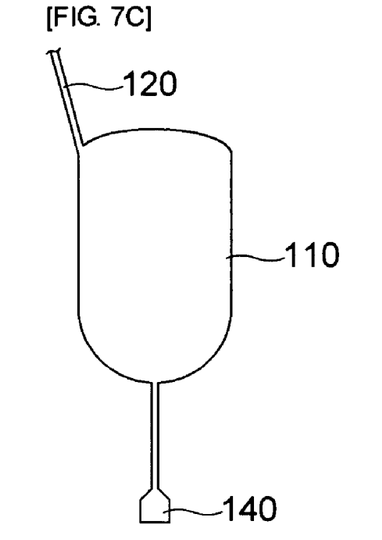

As shown in the cross-sectional views of FIGS. 6 and 7, the ball 130 and the fluid F are inputted into the chamber 110 formed in the upper and lower thin-films 101 and 102. At this time, a diameter d of the ball moving in the chamber 110 is smaller than a height H of the chamber 110 and is larger than a height h of the path 120 for connecting the chambers 110.

That is, it is preferable that the ball 130 is smoothly moved by the centrifugal force and inertia in the chamber 110 and outer surfaces of both ends of the path 120 are composed of slopes 121. At this time, an outer circumference surface of the ball 130 is formed in curvature to be in close contact with the slopes 121.

Meanwhile, as shown in FIGS. 7A to 7C, the path 120 for connecting the chambers 110 is designed to have a height smaller than the height of the chamber 110 by upper and lower stepped portions 122 and 123 having the slopes 121. At this time, a height of the lower stepped portion 123 is preferably lower than a height of the upper stepped portion 122.

The heights of the stepped portions 122 and 123 are different from each other and the height of the lower stepped portion 123 is smaller than the height of the upper stepped portion 122 so as to smoothly the fluid F contained in each chamber 110 at the time of the rotation of the rotating body 100.

Next, FIGS. 7A to 7C are plan views illustrating a form of a chamber which can be applied to the sample analyzing apparatus according to the invention.

As shown in the figure, the chamber 110 formed in the sample analyzing apparatus according to the invention is formed in a triangle (shown in FIG. 7A) including an equilateral triangle, a rectangle (shown in FIG. 7B), or an oval (shown in FIG. 7C).

Corners of the chamber 110 to which the path 120 is connected are formed at 90 degrees or the acute angle of 90 degrees or less. Accordingly, when the ball 130 moves to the corners in the chamber 110 at the time of the rotation of the rotating body 100, the surface of the ball 130 can be fixed while rotating in a state when the surface of the ball 130 is in close contact with the aperture 111 formed on each corner.

In case that the corner of the chamber 110 is formed at an obtuse angle larger than 90 degrees, that is, the corner of the chamber 110 is formed in a polygon such as a pentagon or a hexagon, the ball 130 may be separated along a side extending from the corner.

Figure 8A:
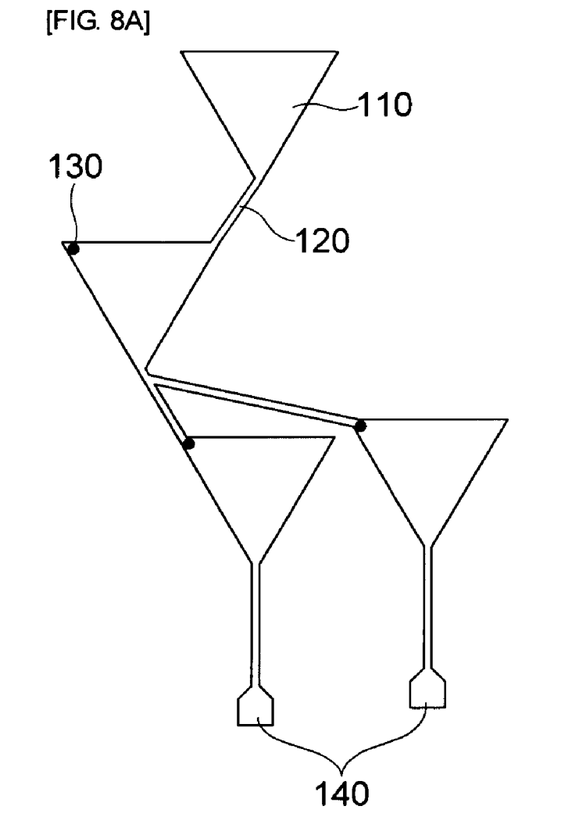
FIGS. 8A and 8B are diagrams illustrating a configuration embodiment of the chamber formed in the sample analyzing apparatus according to the invention.
Figure 8B:
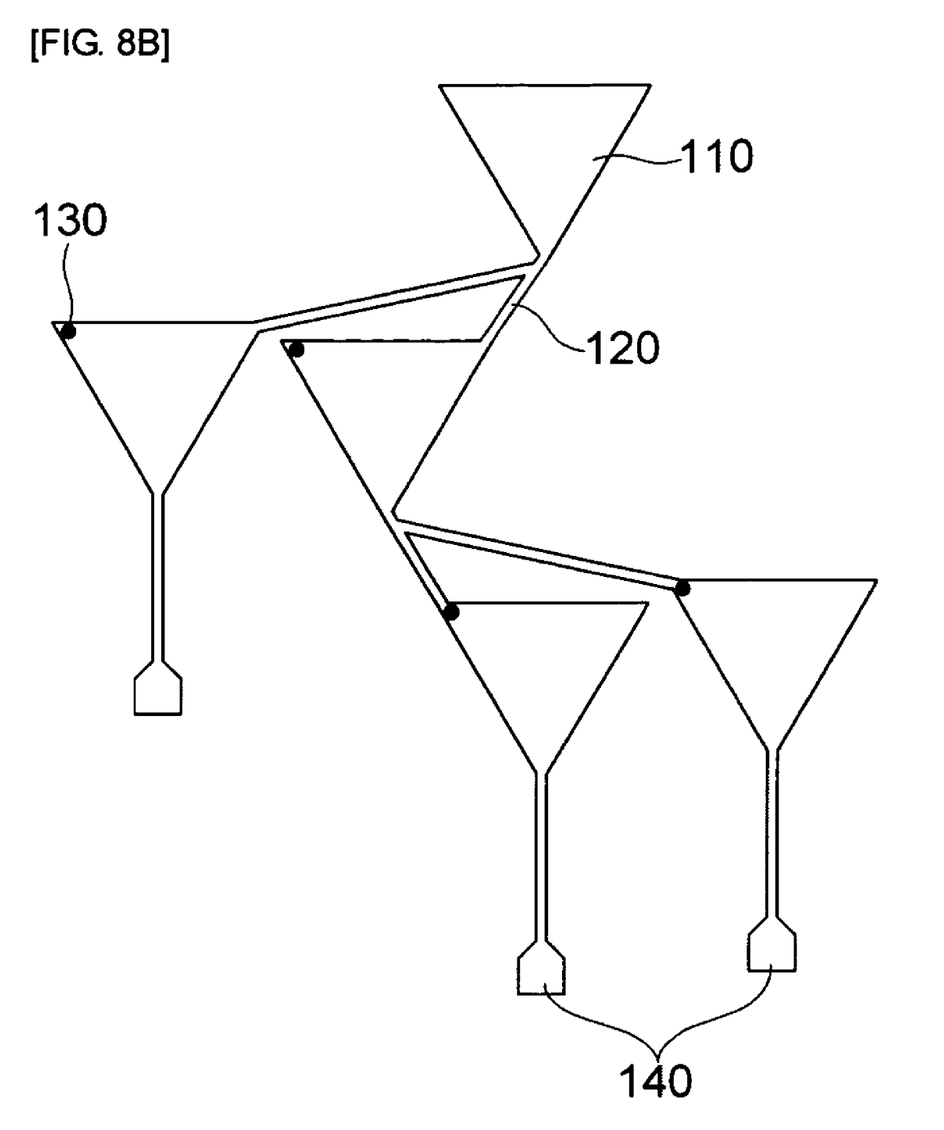

Next, FIGS. 8A and 8B are drawings illustrating a configuration embodiment of the chamber formed in the sample analyzing apparatus according to the invention. As shown in the figure, the plural chambers 110 can be connected to a bottom portion of the chamber 110 formed in the rotating body 100 through the corresponding paths 120 and the fluids inputted into through the sample inputting holes 140 connected to the chamber 110 are mixed in the upper chamber 110 through the opening of the path 120 by the rotation of the rotating body 100.

By these configurations of the chambers 110, the fluids having different samples incorporated in the lower chamber 110 can be mixed in the upper chamber 110.

As described above, since the sample analyzing apparatus using the centrifugal force and inertia according to the invention does not require a separate device by opening and closing the path only by the centrifugal force generated in the chamber by the rotation of the rotating body and the inertia of the ball, the sample analyzing apparatus can be formed in a thin-film and a failure rate can be reduced by a simple technical configuration.

Since the sample analyzing apparatus according to the invention is formed only of the rotating body provided with the chamber and the ball, it is possible to lower manufacturing cost by manufacturing the sample analyzing apparatus at a minimum cost.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A sample analyzing apparatus using centrifugal force and inertia, comprising:
    a rotating body comprised of a disk including upper and lower films;
    first and second chambers, adjacent to each other and each comprising a polygonal space in the rotating body and including apertures on one corner and a bottom side thereof;
    paths connected to the apertures of the first and second chambers to transfer fluids mixed or separated in the chambers;
    sample inputting holes connected to the chambers formed inside of the rotating body through the paths; and
    at least two balls moving respectively within the first and second chambers,
    the first and second chambers being connected to each other in series via the respective path connected between the apertures, the apertures being formed on opposite corners of each respective chamber, whereby when the aperture of the first chamber is opened, the aperture of the second chamber is closed.

2. The sample analyzing apparatus using the centrifugal force and the inertia according to claim 1, wherein the rotating body is made of a polycarbonate substrate including a reflection coating layer on a surface of the polycarbonate substrate.

3. The sample analyzing apparatus using the centrifugal force and the inertia according to claim 1, wherein a height of the path connecting the first and second chambers is smaller than that of the first and second chambers.

4. The sample analyzing apparatus using the centrifugal force and the inertia according to claim 1, wherein the first and second chambers are individually connected to vertical lower parts of the first and second chambers.

5. The sample analyzing apparatus using the centrifugal force and the inertia according to claim 1, wherein one of the first and second chambers comprises an oval.

6. The sample analyzing apparatus using the centrifugal force and the inertia according to claim 1, wherein each of the first and second chambers is formed in a polygon and the space includes a predetermined height between the upper and lower films of the rotating body.

7. The sample analyzing apparatus using the centrifugal force and the inertia according to claim 6, wherein one of the first and second chambers comprises any one polygon of a triangle, and a rectangle, and one or more corners among the corners at one side of the one of the chambers are equipped with corresponding apertures, respectively.

8. The sample analyzing apparatus using the centrifugal force and the inertia according to claim 7, wherein the corner of the one of the chambers is formed at an acute angle.

9. The sample analyzing apparatus using the centrifugal force and the inertia according to claim 1, wherein the balls are moved to the corners in the respective chamber by centrifugal force generated in the respective chamber from rotation of the rotating body and the inertia generated in accordance with masses of the balls.

10. The sample analyzing apparatus using the centrifugal force and the inertia according to claim 9, wherein a diameter of the ball is smaller than the height of the respective chamber and larger than the height of the path.

11. The sample analyzing apparatus using the centrifugal force and the inertia according to claim 10, wherein the ball has a mass larger than the fluid inserted into the respective chamber.

12. The sample analyzing apparatus using the centrifugal force and the inertia according to claim 10, wherein an outer circumference surface of the ball is formed in curvature to be in close contact with the slopes.

13. The sample analyzing apparatus using the centrifugal force and the inertia according to claim 1, wherein upper and lower stepped portions of the path are formed relative to the respective chamber and a height of the upper stepped portion is smaller than that of the lower stepped portion.

14. The sample analyzing apparatus using the centrifugal force and the inertia according to claim 13, wherein outer surfaces of both ends of the path are comprised of slopes.

15. The sample analyzing apparatus using the centrifugal force and the inertia according to claim 14, wherein an outer circumference surface of the ball is formed in curvature to be in close contact with the slopes.

* * * * *